United States Patent
Giannasi et al.

(10) Patent No.: US 11,645,307 B1
(45) Date of Patent: May 9, 2023

(54) METHOD AND APPARATUS FOR GROUPING RECORDS BASED UPON A PREDICTION OF THE CONTENT OF THE RECORDS

(71) Applicant: Change Healthcare Holdings, LLC, Nashville, TN (US)

(72) Inventors: Nick Giannasi, Truckee, CA (US); Rolland Ho, San Francisco, CA (US); Adrian Lam, Emeryville, CA (US); Elsie Qureshi, Walnut Creek, CA (US); Adam Sullivan, Walnut Creek, CA (US)

(73) Assignee: Change Healthcare Holdings, LLC, Nashville, TN (US)

( * ) Notice: Subject to any disclaimer, the term of this patent is extended or adjusted under 35 U.S.C. 154(b) by 647 days.

(21) Appl. No.: 16/213,441

(22) Filed: Dec. 7, 2018

Related U.S. Application Data

(60) Provisional application No. 62/766,590, filed on Oct. 11, 2018.

(51) Int. Cl.
| | |
|---|---|
| *G06F 16/30* | (2019.01) |
| *G06F 16/28* | (2019.01) |
| *G06N 20/00* | (2019.01) |
| *H04L 67/10* | (2022.01) |
| *G16H 10/60* | (2018.01) |
| *G06N 5/04* | (2023.01) |

(52) U.S. Cl.
CPC .......... *G06F 16/285* (2019.01); *G06N 5/04* (2013.01); *G06N 20/00* (2019.01); *G16H 10/60* (2018.01); *H04L 67/10* (2013.01)

(58) Field of Classification Search
CPC .................................................... G06F 16/285
See application file for complete search history.

(56) References Cited

U.S. PATENT DOCUMENTS

| | | | |
|---|---|---|---|
| 2007/0226211 A1* | 9/2007 | Heinze | G16H 50/70 |
| 2008/0077443 A1* | 3/2008 | Singer | G16H 10/60 |
| | | | 705/3 |
| 2016/0048643 A1* | 2/2016 | Woods | G06F 19/00 |
| | | | 705/3 |
| 2016/0358284 A1* | 12/2016 | Bagley | G06Q 50/22 |
| 2019/0189253 A1* | 6/2019 | Kartoun | G16H 10/60 |

\* cited by examiner

*Primary Examiner* — Khanh B Pham
(74) *Attorney, Agent, or Firm* — Myers Bigel, P.A.

(57) ABSTRACT

A method, apparatus and computer program product group records based upon a prediction of the content of the records. In the context of a method, data associated with respective subjects of the records is received and a threshold of a machine learning model is adjusted to satisfy an accuracy requirement for record categorization. In response to analyzing the data, but not the records, by the machine learning model, the method separates, using the machine learning model, the records into the first and second groups with the first group including records that the associated data indicates are more likely to support the addition of a code and the second group including records that the associated data indicates are less likely to support the addition of a code. The method also includes subsequently processing the records in different manners depending upon whether the records are included in the first or second group.

20 Claims, 5 Drawing Sheets

US 11,645,307 B1

METHOD AND APPARATUS FOR GROUPING RECORDS BASED UPON A PREDICTION OF THE CONTENT OF THE RECORDS

CROSS-REFERENCE TO RELATED APPLICATIONS

This application claims priority to U.S. Provisional Application No. 62/766,590, filed Oct. 11, 2018, the entire contents of which are incorporated herein by reference.

TECHNOLOGICAL FIELD

An example embodiment relates generally to a method, apparatus and computer program product for grouping records and, more particularly, to a method, apparatus and computer program product for grouping records based upon a prediction of the content of the records without having to analyze the content of the records.

BACKGROUND

Records, such as electronic records, are generated in large numbers in a wide variety of different industries. For example, records are generated for a variety of business or commercial purposes and medical records are generated that detail at least portions of the medical history of a patient. In a variety of circumstances, some or all of the records are to be audited. The records may be audited for various reasons including audits that are conducted to verify the validity or accuracy of the records and/or to determine whether a record is complete or, instead, needs to be supplemented. Such audits may be time consuming and resource intensive and the challenges with conducting timely audits may be exacerbated by the manner in which records are generated or received. In this regard, the records are not necessarily generated or received at a steady rate, but, instead, large amounts of records may be generated or received during one time period and many fewer records may be generated or received during another time period, thereby further complicating the performance of a timely audit.

BRIEF SUMMARY

A method, apparatus and computer program product are provided in accordance with an example embodiment in order to utilize a trained machine learning model to group records based upon a prediction of the content of the records. By grouping the records based upon a prediction of the content, the content itself need not be substantively reviewed in order to group the records with the grouping, instead, being based upon data associated with the records, such as data associated with the subject of a record. Consequently, the method, apparatus and computer program product of an example embodiment is configured to group the records in a more efficient manner than if the content of the records were to be substantively reviewed. The different groups of records can then be differently processed, such as by assigning audit responsibility to different auditors, thereby resulting in enhanced efficiency in the overall processing of the record and a corresponding conservation of resources including computational resources and time that is expended during the grouping of the records.

In an example embodiment, a method is provided for grouping records based upon a prediction of the content of the records. The method includes receiving data associated with respective subjects of the records. The method also includes inputting the data, but not the records, into a machine learning model for a prediction as to whether respective records support the addition of a code. The method further includes adjusting one or more thresholds utilized by the machine learning model in conjunction with the prediction as to whether respective records support the addition of the code in order to satisfy an accuracy requirement for categorization of the records. In response to the predictions attributable to analyzing the data, but not the records, by the machine learning model, the method separates, using the machine learning model, the records into the first and second groups with the first group including the records that the associated data indicates are more likely to support the addition of the code and the second group including the records that the associated data indicates are less likely to support the addition of a code. The method also includes providing for subsequent processing of the records with the subsequent processing differing depending upon whether the records are included in the first group of records or in the second group of records.

The method of an example embodiment provides for subsequent processing of the records by assigning, by audit assignment circuitry, different audit responsibility for the records depending upon whether the records are included in the first group of records or the second group of records. The method of this example embodiment assigns different audit responsibility by assigning audit responsibility for the first and second groups of records to first and second auditors, respectively. In an example embodiment, the method also includes receiving results from the separate auditing of the first and second groups of records and, in response to the results from the auditing, modifying, by record modification circuitry, at least one of the records to be associated with the code.

The method of an example embodiment also includes splitting the records into multiple partitions across a distributed computing framework. In this example embodiment, the method also includes placing the machine learning model on each of a plurality of nodes of the distributed computing framework such that the machine learning model on a respective node analyzes records in a respective partition.

In an example embodiment, the records include medical records and the code includes a hierarchical condition category (HCC) code. In this example embodiment, the data includes payor data from one or more healthcare providers that includes one or more of claims information or summarized encounter information. The method of this example embodiment may also exclude, by filtration circuitry, Medicare records from consideration prior to inputting the data into a machine learning model.

In another example embodiment, an apparatus is provided for grouping records based upon a prediction of the content of the records. The apparatus includes input circuitry configured to receive data associated with respective subjects of the records for a prediction as to whether respective records support the addition of a code. That apparatus also includes a machine learning model configured to adjust one or more thresholds utilized by the machine learning model in conjunction with the prediction as to whether respective records support the addition of the code in order to satisfy an accuracy requirement for categorization of the records. The machine learning model is further configured to analyze the data, but not the records, and to separate the records into first and second groups. The first group includes the records that the associated data indicates are more likely to support the addition of the code and the second group includes the records that the associated data indicates are less likely to support the addition of the code. The apparatus further includes processing circuitry configured to provide for subsequent processing of the records. The subsequent processing differs dependent upon whether the records are included in the first group of records or the second group of records.

The processing circuitry configured to provide for subsequent processing of the records includes audit assignment circuitry configured to assign different audit responsibility for the records depending upon whether the records are included in the first group of records or the second group of records. The audit assignment circuitry of an example embodiment is configured to assign different audit responsibility by assigning audit responsibility for the first and second groups of records to first and second auditors, respectively. The apparatus of this example embodiment also includes record modification circuitry configured to receive results from separately auditing the first and second groups of records and, in response to the results from the auditing, to modify at least one of the records to be associated with the code.

The apparatus of an example embodiment is embodied by a distributed computing framework. In this embodiment, the input circuitry is configured to split the records into multiple partitions across the distributed computing framework. In addition, the machine learning model of this embodiment is placed on each of a plurality of nodes of the distributed computing framework such that the machine learning model on a respective node analyzes records in a respective partition.

The records of an example embodiment include medical records and the code includes a hierarchical condition category (HCC) code. In this example embodiment, the data may include payor data from one or more healthcare providers that includes one more of claims information or summarized encounter information. The apparatus of this example embodiment may also include filtration circuitry configured to exclude Medicare records from consideration prior to inputting the data into the machine learning model.

In a further example embodiment, a computer program product is provided that includes at least one non-transitory computer readable storage medium for grouping records based upon a prediction of the content of the records. The at least one non-transitory computer-readable storage software instructions that, when executed, cause an apparatus to receive data associated with respective subjects of the records. The software instructions, when executed, also cause the apparatus to input the data, but not the records, into a machine learning model for a prediction as to whether respective records support the addition of a code. The software instructions, when executed, also cause the apparatus to adjust one or more thresholds utilized by the machine learning model in conjunction with the prediction as to whether respective records support the addition of the code in order to satisfy an accuracy requirement for categorization of the records. The software instructions, when executed, further cause the apparatus, in response to the predictions attributable to analyzing the data, but not the records, by the machine learning model, to separate, using the machine learning model, the records into first and second groups. The first group includes the records that the associated data indicates are more likely is to support addition of the code. The second group includes the records that the associated data indicates are less likely to support the addition of the code. The software instructions, when executed, additionally cause the apparatus to provide for subsequent processing of the records with the subsequent processing differing dependent upon whether the records are included in the first group of records or the second group of records.

The software instructions that, when executed, cause the apparatus to provide for subsequent processing of the records may include software instructions that, when executed, cause the apparatus to assign different audit responsibility for the records depending upon whether the records are included in the first group of records or the second group of records. The software instructions that, when executed, cause the apparatus to assign different audit responsibility may include software instructions that, when executed, cause the apparatus to assign audit responsibility for the first and second groups of records to first and second auditors, respectively. In an example embodiment, the software instructions, when executed, further cause the apparatus to receive results from separately auditing the first and second groups of records and, in response to the results from the auditing, modify at least one of the records to include the code. The records of an example embodiment include medical records and the code includes a hierarchical condition category (HCC) code. The data of this example embodiment may include payor data from one or more healthcare providers that includes one or more of claims information or summarized encounter information.

The software instructions, when executed, also cause the apparatus to split the records into multiple partitions across a distributed computing framework. In this example embodiment, the software instructions, when executed, also cause the apparatus to place the machine learning model on each of a plurality of nodes of the distributed computing framework such that the machine learning model on a respective node analyzes records in a respective partition.

The above summary is provided merely for purposes of summarizing some example embodiments to provide a basic understanding of some aspects of the invention. Accordingly, it will be appreciated that the above-described embodiments are merely examples and should not be construed to narrow the scope or spirit of the invention in any way. It will be appreciated that the scope of the invention encompasses many potential embodiments in addition to those here summarized, some of which will be further described below.

BRIEF DESCRIPTION OF THE DRAWINGS

Having described certain example embodiments of the present disclosure in general terms above, reference will now be made to the accompanying drawings, which are not necessarily drawn to scale and wherein.

DETAILED DESCRIPTION

Some embodiments of the present disclosure will now be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout. As used herein, the terms "data," "content," "information," and similar terms may be used interchangeably to refer to data capable of being transmitted, received, and/or stored in accordance with embodiments of the present invention. Thus, use of any such terms should not be taken to limit the spirit and scope of embodiments of the present invention.

A method, apparatus and computer program product are provided for utilizing a trained machine learning model to group records based upon a prediction of the content of the records. By grouping the records based upon the prediction of the content of the records, but without substantive review of the content of the records, the grouping of the records can be performed in a more computationally efficient manner than if the content of the records were substantively review. As such, the method, apparatus and computer program product of an example embodiment conserve computational resources and time. Once grouped, the method, apparatus and computer program product of an example embodiment provide for subsequent processing of the records with the subsequent processing differing depending upon the group into which the records have been placed. Thus, the subsequent processing of the records may be tailored based upon the prediction of the content of the records as reflected by the grouping of the records.

Figure 1:
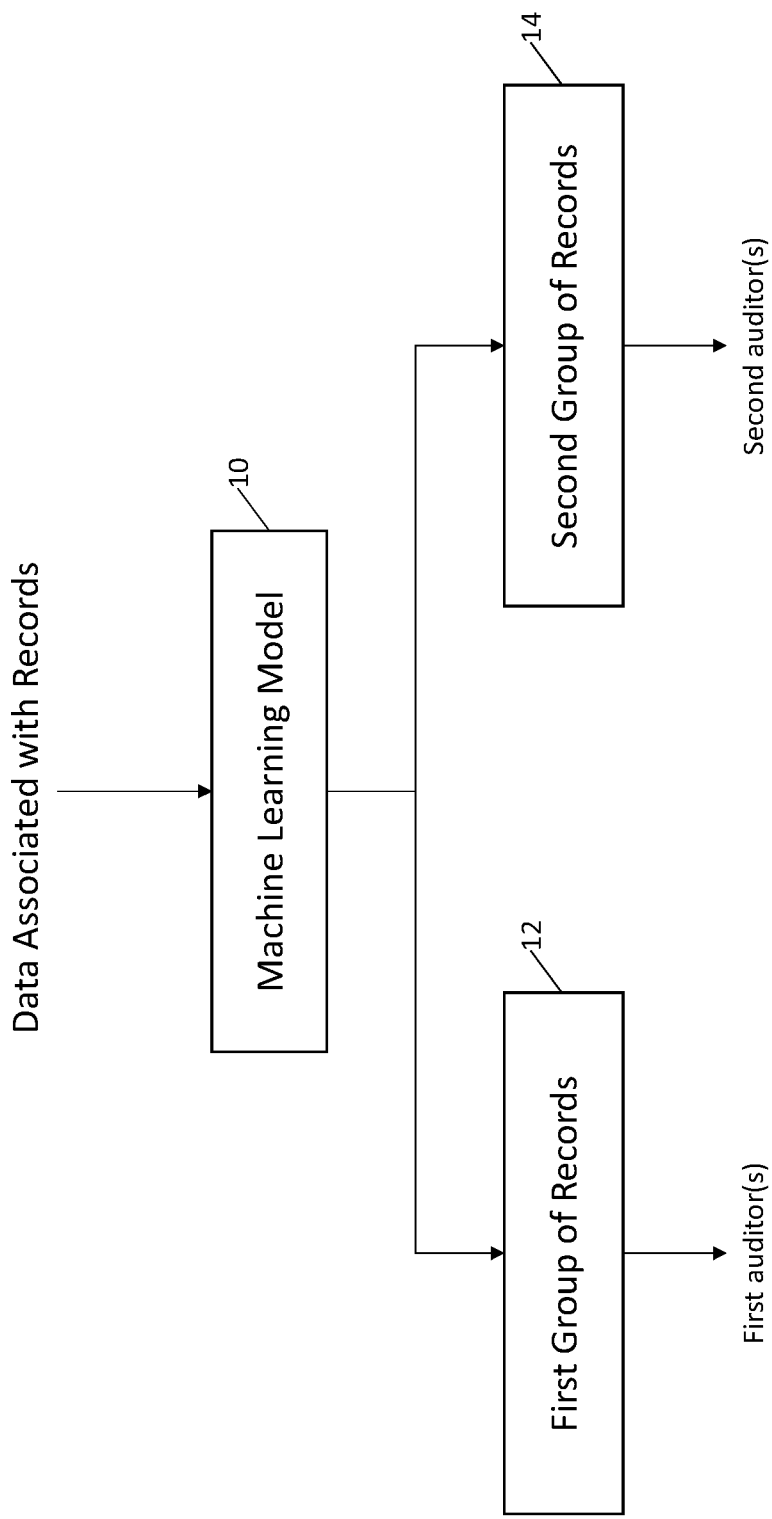
FIG. 1 illustrates the grouping of the records by a machine learning model based upon data associated with the records in accordance with an example embodiment of the present disclosure.

Referring now to FIG. 1, an overview of the manner in which the records are separated into groups is illustrated. As shown, data associated with the records is provided to a machine learning model 10. The machine learning model separates the records into a plurality of groups of records including, at a minimum, first and second groups of records 12, 14. As indicated by the provision of the data associated with the records to the machine learning model, the grouping provided by the machine learning model is based upon the data associated with the records from which a prediction of the content of the records is derived. However, the grouping is not based upon a review of the actual content of the records and, in some embodiments, the records themselves are not provided to the machine learning model with the machine learning model being instead provided only data associated with the records, such as data associated with the subjects of the records, such that the grouping of the records is performed in a more computationally efficient manner so as to conserve computational resources and time than if the content of the records were substantively considered.

As described below, once separated into first and second groups 12, 14 as shown in FIG. 1, the records are subjected to subsequent processing that differs depending upon the group to which the records belong. Although the records may be subjected to a variety of different types of processing following the grouping of the records, the method, apparatus and computer program product of an example embodiment differently process the groups of records by assigning different audit responsibility for the records depending upon the group to which the records belong. As shown in FIG. 1, for example, the first group of records may be assigned to first auditor(s), while the second group of records is assigned to second auditor(s). As the groups of records are based upon a prediction of the content of the records, the groups of records are differently processed, such as by being assigned to different auditors, based upon the prediction of the content of the records as opposed to a substantive review of the content of the records themselves. The auditors to which a group of records is assigned may be particularly qualified or better qualified for auditing the records of the respective group than the other auditors. As such, the resulting performance brought about by the additional processing of the records may be enhanced by conditioning the additional processing based upon the grouping of the records. For example, the assignment of auditing responsibility for the records to a group that is more proficient or better qualified to review the records in question may permit the auditing to be performed more efficiently and/or with higher quality.

The method, apparatus computer program product may be configured to group a variety of different types of records. In an example embodiment, the method, apparatus computer program product are configured to group medical records, such as the electronic medical records (EMRs), of a plurality of patients. The electronic medical records may include information regarding the patient as well as detailed information regarding various encounters that the patient has had with one or more healthcare practitioners.

The medical records may be grouped in various manners. In an example embodiment, however, medical records that fail to include a code, such as a hierarchical condition category (HCC) code, are grouped depending upon the likelihood that the code, e.g., an HCC code, should have actually been included in or associated with the respective medical record. A plurality of HCC codes have been defined with each HCC code associated with a disease group of acute or chronic medical condition(s). Examples of disease groups for which HCC codes have been defined include major depressive and bipolar disorders, asthma and pulmonary disease, diabetes, specified heart arrhythmias, congestive heart failure, breast and prostate cancer, rheumatoid arthritis, and colorectal and kidney cancer. HCC codes for related condition categories are defined in a hierarchical manner with a patient having two or more related condition categories only being associated with the HCC code for the most severe manifestation of the related diseases. HCC codes are utilized by a risk adjustment model introduced by the Centers for Medicare and Medicaid Service (CMS) and now also used by the Department of Health and Human Services (HHS) that provides payment to healthcare benefit plans, including Medicare benefit plans and commercial healthcare benefit plans, respectively, based upon the health expenditure risk of their enrollees. By conditioning the payments to the healthcare benefit plans upon the HCC codes of the enrollees of the respective healthcare benefit plans, a healthcare benefit plan may be paid appropriately for their expected relative costs with healthcare benefit plans that care for more enrollees associated with an HCC code being paid more, on average, than healthcare benefit plans having enrollees that are not associated with HCC codes.

In practice, some medical records of patients that should be associated with an HCC code as a result of the acute or chronic medical condition(s) experienced by the patient may not be appropriately coded so as to be associated with the HCC code. As such, the healthcare benefit plan of the patient may not be appropriately compensated for the anticipated medical expenses incurred by the patient. As such, the healthcare benefit plans, including the federal government in terms of Medicare benefit plans and insurance companies in terms of commercial healthcare benefit plans, may sometimes review the medical records in an effort to identify any medical records associated with a patient that should be associated with an HCC code, but that have not been appropriately coded such that the healthcare benefit plan has not been appropriately reimbursed for the anticipated medical expenses of the patient. In an instance in which a medical record is identified that should have been associated with an HCC code, the medical record may be supplemented, e.g., modified, so as to include the appropriate HCC code.

However, individual medical records are frequently sizeable and the number of medical records is substantial and growing rapidly. As such, auditing of the medical records may be a time consuming and resource intensive exercise that may require the services of many auditors to review the medical records. However, not every auditor is as experienced, skillful or proficient such that the performance of the auditors varies appreciably with some auditors consistently identifying those records that should be associated with an HCC code, while other auditors fail to identify the medical records that should be associated with an HCC code in as consistent of a manner. Thus, even after being audited, medical records may not be supplemented in as consistent of a manner as would be desired so as to associate HCC codes with those medical records of patients having acute or chronic medical condition(s) that qualify for an HCC code since some auditors, e.g., the more poorly performing auditors, may fail to consistently identify those medical records that lack an HCC code, but that should actually be associated with an HCC code. Consequently, a healthcare benefit plan may not be reimbursed to the same degree as if each of the medical records that should be associated with an HCC code were correctly coded, either initially or following a modification brought about by the auditing process.

In order to increase the consistency with which medical records that should be associated with a code, such as an HCC code, are identified, the method, apparatus and computer program product of an example embodiment utilize a machine learning model to group the records based upon the likelihood of the records supporting the addition of a code, such as an HCC code. Those records that are more likely to support the addition of a code, such as an HCC code, may form a first group of records which may, in turn, be assigned to a first group of one or more auditors, while a second group of records that are less likely to support the addition of a code, such as an HCC code, may be assigned to a second group of one or more auditors. The first group of auditors may be the auditors that perform better such as due to experience, training or otherwise. By assigning the medical records that do not include a code, such as an HCC code, but that are more likely to support the addition of a code, such as an HCC code, to the auditors that offer better performance, the likelihood that medical records that should support the addition of a code, such as an HCC code, will be identified by the auditors and modified to be associated with a code, such as an HCC code, is increased, thereby resulting in a corresponding and appropriate increase in the amount by which a healthcare benefit plan is funded. By assigning the other records that are less likely to support the addition of a code, such as an HCC code, to a second group of auditors who do not perform as well as the first group of auditors, the risk associated with the second group of auditors failing to identify a medical record that should be associated with a code, such as an HCC code, is significantly reduced since even though the performance of the second group of auditors is less consistent, the percentage of the records that the second group of auditors is reviewing that should associated with a code, such as an HCC code, is less than the records analyzed by the first group of auditors. While the grouping of the records into first and second groups is described above, the records may be separated into more groups in other embodiments with the separation into first and second groups being provided by way of example, but not of limitation.

The apparatus of an example embodiment may be embodied by any of a variety of devices. Example embodiments may include a plurality of networked devices operating in a distributed system. In this regard, it will be understood that the term "distributed system" refers to a plurality of networked devices in which some components are shared among the devices. Whether or not the invention is implemented using a distributed system or not, example devices embodying embodiments described herein may comprise any of a variety of fixed terminals, such as servers, desktop computers, mainframe devices, kiosks, or the like. Such example devices may additionally or alternatively comprise any of a variety of mobile terminals, such as portable digital assistants (PDAs), mobile telephones, smartphones, laptop computers, tablet computers, or any combinations of the aforementioned devices.

Figure 2:
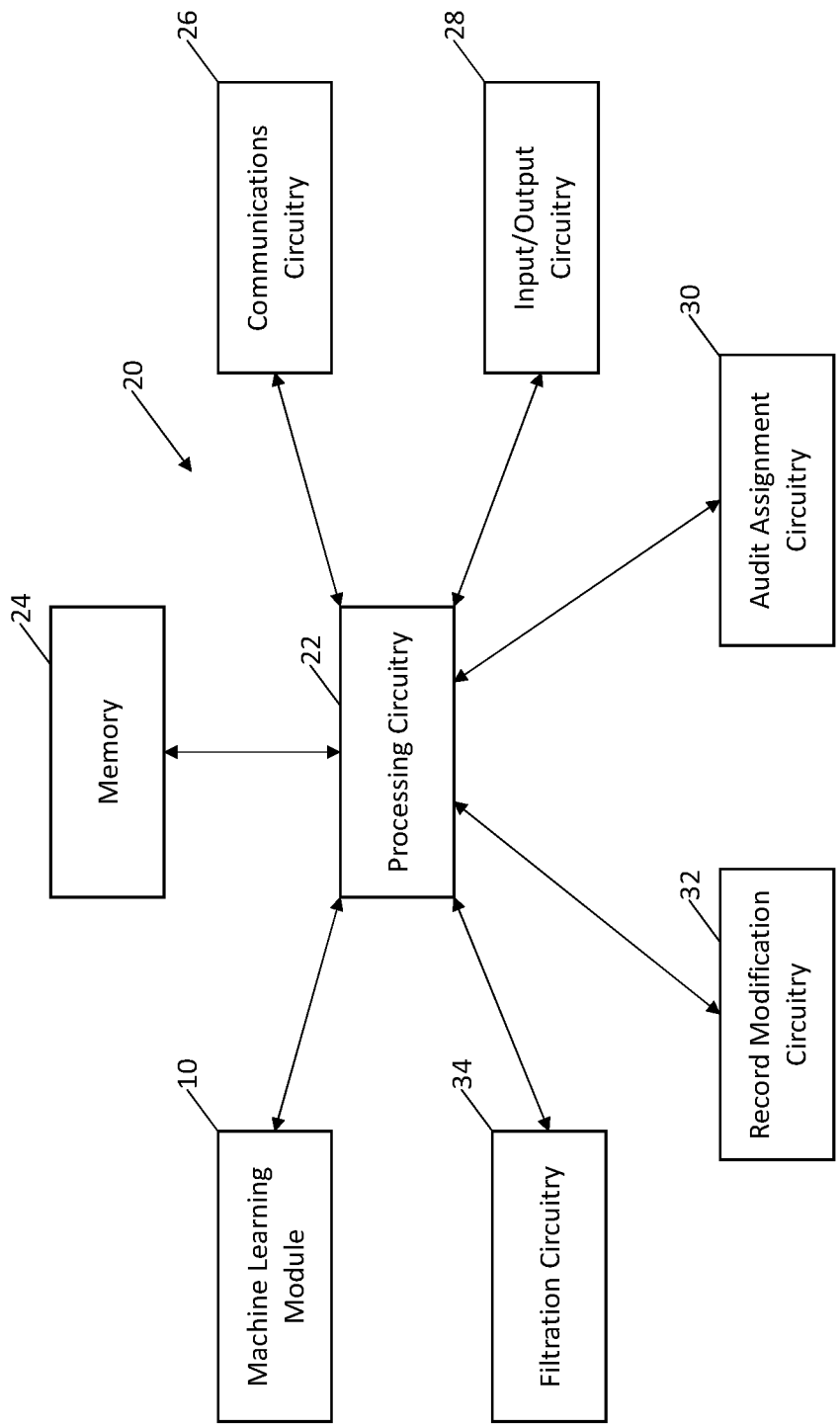
FIG. 2 is a block diagram of an apparatus that may be specifically configured in accordance with an example embodiment of the present disclosure.

Turning to FIG. 2, an example apparatus 20 is illustrated that may be configured to perform the operations described herein. The apparatus 20 includes a processing circuitry 22, a memory 24, and communications circuitry 26. The apparatus also includes audit assignment circuitry 30, record modification circuitry 32, filtration circuitry 34, and machine learning model 10, which will be described in greater detail below. The apparatus may further include input/output circuitry 28 in some embodiments to facilitate user interaction (input/output circuitry is optional in some embodiments, however, insofar as those embodiments do not require a direct interface between the apparatus and a user). The apparatus may be configured to execute the operations described below in connection with FIGS. 3 and 5.

In some embodiments, the processing circuitry 22 may be in communication with the memory 24 via a bus for passing information among components of the apparatus. The processing circuitry may be embodied in a number of different ways and may, for example, include one or more processing devices configured to perform independently. Additionally or alternatively, the processing circuitry may include one or more processors configured in tandem via a bus to enable independent execution of software instructions, pipelining, and/or multithreading. The use of the terms "processor" or "processing circuitry" may be understood to include a single core processor, a multi-core processor, multiple processors of the apparatus 20, remote or "cloud" processors, or any combination thereof.

In an example embodiment, the processing circuitry 22 may be configured to execute software instructions stored in the memory 24 or otherwise accessible to the processing circuitry. Alternatively or additionally, the processing circuitry may be configured to execute hard-coded functionality. As such, whether configured by hardware or software methods, or by a combination of hardware with software, the processing circuitry may represent an entity (e.g., physically embodied in circuitry) capable of performing operations according to an embodiment of the present invention while configured accordingly. Alternatively, as another example, when the processing circuitry is embodied as an executor of software instructions, the software instructions may specifically configure the processing circuitry to perform the algorithms and/or operations described herein when the software instructions are executed.

Memory 24 is non-transitory and may include, for example, one or more volatile and/or non-volatile memories. In other words, for example, the memory may be an electronic storage device (e.g., a computer readable storage medium). The memory may be configured to store information, data, content, applications, software instructions, or the like, for enabling the apparatus 20 to carry out various functions in accordance with example embodiments contemplated herein.

The communications circuitry 26 may be any means such as a device or circuitry embodied in either hardware or a combination of hardware and software that is configured to receive and/or transmit data from/to a network and/or any other device, circuitry, or module in communication with the apparatus 20. In this regard, the communications circuitry may include, for example, a network interface for enabling communications with a wired or wireless communication network. For example, the communications circuitry may include one or more network interface cards, antennas, buses, switches, routers, modems, and supporting hardware and/or software, or any other device suitable for enabling communications via a network. Additionally or alternatively, the communication interface may include the circuitry for causing transmission of such signals to a network or to handle receipt of signals received from a network.

In some embodiments, the apparatus 20 may optionally include input/output circuitry 28 in communication configured to provide output to a user and, in some embodiments, to receive an indication of user input. The input/output circuitry may comprise a user interface, such as a display, and may further comprise the components that govern use of the user interface, such as a web browser, mobile application, dedicated client device, or the like. In some embodiments, the input/output circuitry may additionally or alternatively include a keyboard, a mouse, a touch screen, touch areas, soft keys, a microphone, a speaker, and/or other input/output mechanisms. The input/output circuitry may utilize the processing circuitry 22 to control one or more functions of one or more of these user interface elements through software instructions (e.g., application software and/or system software, such as firmware) stored on a memory (e.g., memory 24) accessible to the processing circuitry.

In addition, the apparatus 20 comprises audit assignment circuitry 30, which includes hardware components designed for assigning different audit responsibility for the records depending upon the group in which the records are included. The audit assignment circuitry may utilize processing circuitry 22, memory 24, or any other hardware component included in the apparatus to perform and possibly store the operations described in connection with FIG. 5 below. The audit assignment circuitry may further utilize communications circuitry 26 to transmit results of the audit assignment.

In addition, the apparatus 20 comprises record modification circuitry 32, which includes hardware components designed for modifying at least one of the records to be associated with a code, such as an HCC code. The record modification circuitry may utilize processing circuitry 22, memory 24, or any other hardware component included in the apparatus to perform and possibly store the operations described in connection with FIG. 5 below. The record modification circuitry may further utilize communications circuitry 26 to transmit results of the record modification.

In addition, the apparatus 20 further comprises filtration circuitry 34, which includes hardware components designed for excluding Medicare records from consideration prior to inputting the data into the machine learning model 10 in accordance with various examples described herein. The filtration circuitry may utilize processing circuitry 22, memory 24, or any other hardware component included in the apparatus to perform these filtration operations, as described below.

Finally, the apparatus 20 also comprises a machine learning model 10, which may be trained and utilized in the manner described below in connection with FIGS. 3 and 5. The machine learning model may be executed by processing circuitry 22 and may be hosted on memory 24. The machine learning model may have multiple layers of a variety of types, and as such the machine learning model may comprise a gradient boosted forest model, a random forest model or a tree-based model.

Although these components 10, 30-34 may in part be described using functional language, it will be understood that the particular implementations necessarily include the use of particular hardware. It should also be understood that certain of these components may include similar or common hardware. For example, the audit assignment circuitry 30, record modification circuitry 32, filtration circuitry 34 and machine learning model 10 may each at times leverage use of the processing circuitry 22 or memory 24, but duplicate hardware is not required to facilitate operation of these distinct components of the apparatus 20 (although duplicated hardware components may be used in some embodiments, such as those in which enhanced parallelism may be desired). The use of the term "circuitry" as used herein with respect to components of the apparatus therefore shall be interpreted as including the particular hardware configured to perform the functions associated with the particular circuitry described herein. Of course, while the term "circuitry" should be understood broadly to include hardware, in some embodiments, the term "circuitry" may refer also to software instructions that configure the hardware components of the apparatus to perform their various functions.

To this end, each of the processing circuitry 22, audit assignment circuitry 30, record modification circuitry 32, filtration circuitry 34, and machine learning model 10 may include one or more dedicate processor, specially configured field programmable gate array (FPGA), or application specific interface circuit (ASIC) to perform its corresponding functions, these components may additionally or alternatively be implemented using a processor executing software stored in a memory (e.g., memory 24). In this fashion, the processing circuitry, audit assignment circuitry, record modification circuitry and filtration circuitry are therefore implemented using special-purpose components implemented purely via hardware design or may utilize hardware components of the apparatus 20 that execute computer software designed to facilitate performance of the functions of the processing circuitry, audit assignment circuitry, record modification, filtration circuitry, and machine learning model.

As will be appreciated based on this disclosure, example embodiments contemplated herein may be implemented by apparatus 20. Furthermore, embodiments may take the form of a computer program product on at least one non-transitory computer-readable storage medium (e.g., memory 24) storing software instructions. Any suitable non-transitory computer-readable storage medium may be utilized, some examples of which are non-transitory hard disks, CD-ROMs, flash memory, optical storage devices, and magnetic storage devices. It should be appreciated, with respect to certain devices embodied by apparatus as described in FIGS. 3 and 5, that loading the software instructions onto a computer or apparatus produces a special-purpose machine comprising the means for implementing various functions described herein.

Figure 3:
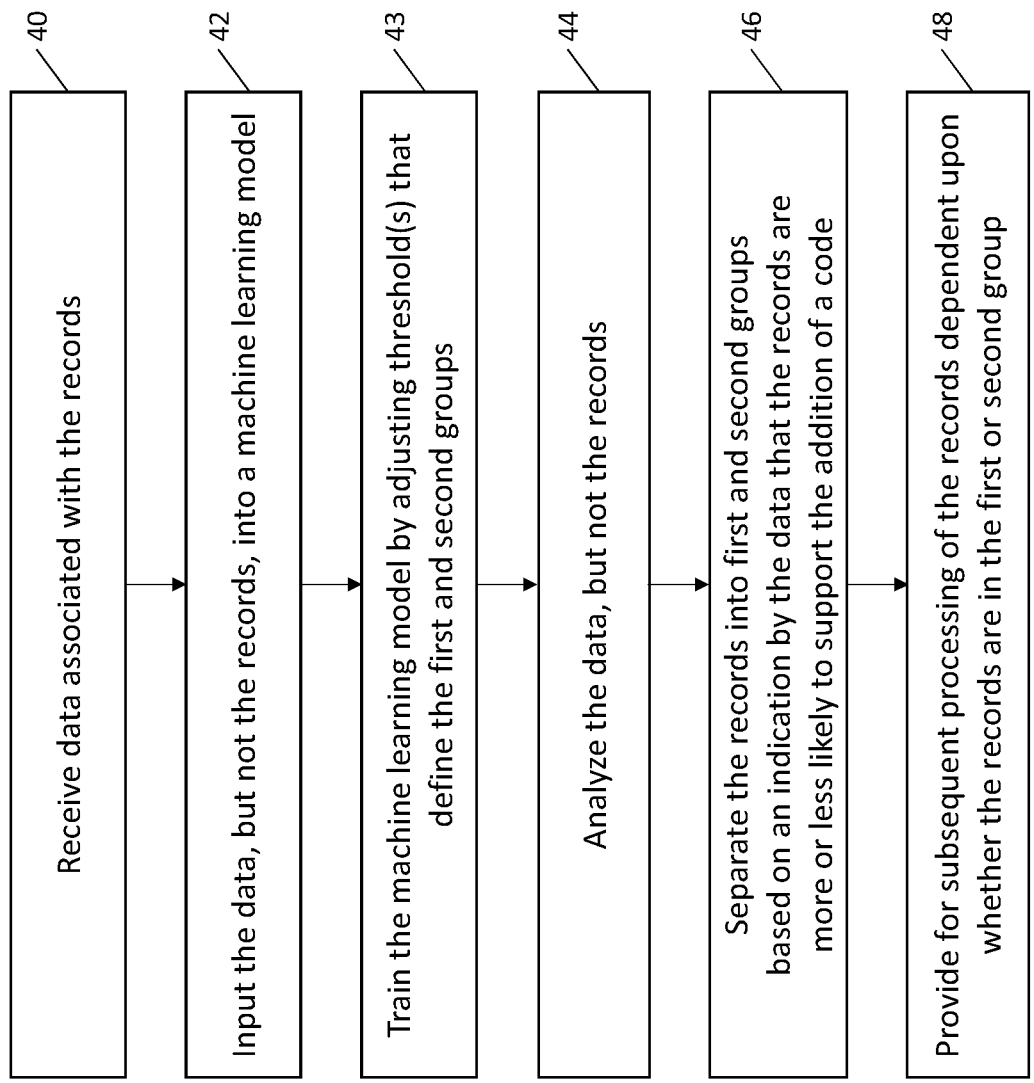
FIG. 3 is a flow chart illustrating the operations performed, such as by the apparatus of FIG. 2, for grouping records based upon a prediction of the content of the records in accordance with an example embodiment of the present disclosure.

Referring now to FIG. 3 which illustrates the operations performed in accordance with an example embodiment and, more particularly, to block 40 of FIG. 3, the apparatus 20 includes means, such as the input/output circuitry 28, communication circuitry 26, the processing circuitry 22 or the like, for receiving data associated with the records. The data that is associated with the records may be associated with respective subjects of the records, such as respective patients of medical records. Additionally or alternatively, the data that is associated with the records need not be associated with the subjects of the records, such as the patient, but may be more general and, in one embodiment, may be related to the provider of healthcare services to which the records relate and/or a disease group to which the records relate. However, the data associated with the record is different than the content of the record itself. In terms of this difference, some or all of the data may also be included in the content of the record, but the data associated with the record is a much smaller amount of data than the content of the record such that the content of the record includes more information, such as substantially more detailed information, than the data associated with the record. In some embodiments, the data associated with the record may be a summary of or otherwise representative of a portion of the content of the record.

In the context of medical records, the data may include payor data that is provided by one or more healthcare providers. This payor data may include claims information, that is, information relating to prior reimbursement claims submitted by a patient, and/or summarized encounter information providing a summary of the different encounters with healthcare professionals that the patient has experienced. Although the data that is provided may vary appreciably in conjunction with various embodiments, data of an example embodiment includes a provider identification (ID), a provider type or specialty, such as radiology, oncology or other specialty, a bill type, a revenue code, a length of service, a surgical procedure code, a medal level provided by an insurance company, a risk view score provided by a payor, the number of claims of the patient in a predefined time period, such as a year, a prescription score, a total disease count, the number of ICD codes, such as ICD-10 codes, associated with the patient and included within the medical record, etc.

As shown in block 42 of FIG. 3, the apparatus 20 includes means, such as the processing circuitry 22 or the like, for inputting the data, but not the records, into a machine learning model 10. By inserting the data, but not the records themselves, the amount of information provided to the machine learning model is less, thereby conserving the computational resources and computational time required to analyze and group the records based upon an analysis of the data. As the data is associated with and, in many instances, representative of the content of the records, the reliance upon the data by the machine learning model increases the likelihood that the records will be appropriately grouped even though the content of the records has not been substantively considered.

Figure 4:
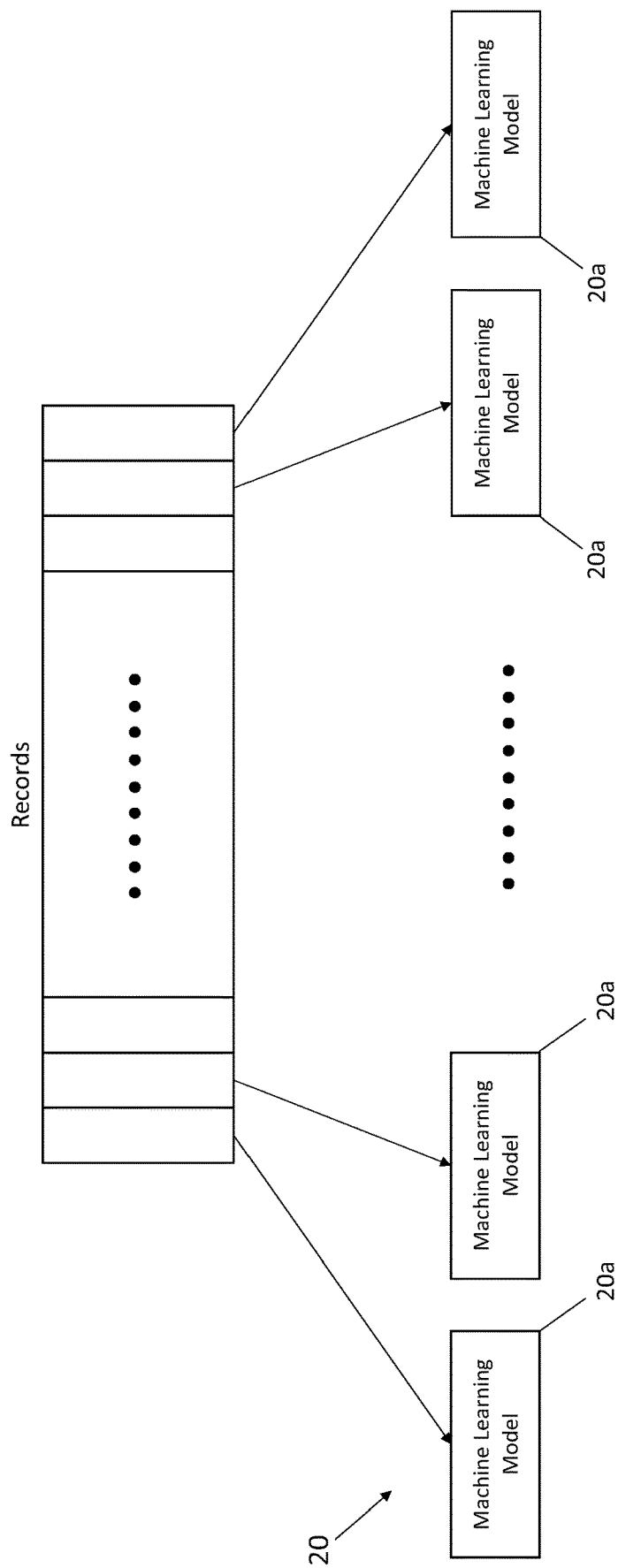
FIG. 4 is a block diagram illustrating the splitting of the records into multiple partitions for processing by a distributed computing framework in accordance with an example embodiment of the present disclosure.

As shown in block 44, the apparatus 20 includes means, such as the machine learning model 10, for analyzing the data, but not the records. Various types of machine learning models may be utilized in order to analyze the data. In an example embodiment, however, the machine learning model is a gradient boosted forest model, while in another embodiment, the machine learning model is a random forest model or a tree-based model. As records themselves are independent in that the prediction of one record does not require information from another record, records can be split, such as by the input circuitry 28, into multiple partitions across a distributed computing framework that embodies the apparatus. See, for example, FIG. 4 in which the records are split into multiple partitions. In this example embodiment, the machine learning model is placed on each of a plurality of nodes 20a of the distributed computing framework, thereby allowing rapid and parallelized predictions across all records which is particularly helpful as the number of records increases, such as in instances in which millions of records are audited. For example, the machine learning model at one node can process the records in one partition, while the machine learning model at another node can process the records in another partition.

As shown in block 46 of FIG. 3 and in response to analyzing the data, but not the records, the apparatus 20 includes means, such as the machine learning model 10 or the like, for separating the records into a plurality of groups, including, at a minimum, first and second groups 12, 14. The machine learning model is trained so as to separate the records into groups based upon the data associated with the records which indicates the likelihood of the underlying records supporting the addition of a code, such as an HCC code. Thus, the first group into which the records are separated includes the records that the associated data indicate are more likely to support the addition of a code, such as an HCC code. Conversely, the second group onto which the records are separated includes the records that the associated data indicates are less likely to support the addition of a code, such as an HCC code. The machine learning model may be trained to separate the records into the first and second groups based upon a threshold above which a record is considered more likely to support the addition of a code, such as an HCC code, and below which a record is considered less likely to support the addition of a code, such as an HCC code. The threshold may be adjusted by a system designer or the trainer of the machine learning model based upon whether records having an intermediate likelihood of supporting the addition of a code, such as an HCC code, are preferred to be included in the first group or the second group of records.

Various features of the training data may be utilized to train the machine learning model 10. For example, a machine learning model may use features from the following categories for training purposes: the principle and secondary diagnoses included in the claim (e.g., diabetes, kidney failure, etc.), the procedures included in the claim (e.g., coronary bypass), the place of service (e.g., in-patient hospital, emergency room, etc.) and/or the type of provider (e.g., cardiology, radiology, etc.). Each category is assigned its own variable. In an example embodiment, categories that appear infrequently, such as by appearing in less than a predefined percentage of claims, may be grouped together into a composite category. The categorized data is fed into the machine learning model to predict whether the record supports the addition of a code, such as an HCC code.

In regards to a tree-based machine learning model, the machine learning model uses a subset of the data, such as categories that the tree-based model considers as the most salient categories for a prediction in order to predict whether the record supports the addition of a code, such as an HCC code. In an embodiment in which the machine learning model employs a gradient boosted forest, tree-based models configured to perform as described above would be constructed in a serial fashion, where each subsequent tree-based model is configured to correct errors from the previous tree-based models, thus repeatedly reducing or minimizing the prediction error. In an embodiment in which the machine learning model employs a random forest, tree-based model configured to perform as described above would be constructed in parallel. The random forest model of an example embodiment is configured to use a bootstrapping process, which randomly samples a subset of the variables that can be used to build a tree-based model and a subset of the training data over which the tree-based model is optimized to learn. Parameters of both the gradient-boosted model or the random forest model, such as the number of tree-based models to build, the depth of the tree-based model, the fraction of the data from which to learn, and/or the size of the subset of variables that can be used to create a tree-based model, can be defined by user-defined values. The data upon which the machine learning model is trained may also be augmented to increase the number of records of the minority class by duplicating the data to force the machine learning model to learn more about records that otherwise appear infrequently.

After training is completed, the machine learning model 10 is configured to output a probability or score that is used to rank the likelihood of the underlying records to support the addition of a code, such as an HCC code. A threshold is defined and the probability or score associated provided by the machine learning model with respect to a record may be compared by the apparatus 20, such as the processing circuitry 22 or the like, to the threshold to separate the records into the first and second groups having a high likelihood and low likelihood, respectively, of the record containing a code. In an example embodiment, first and second thresholds may be defined with the first threshold being greater than the second threshold. A probability or score above the first threshold may indicate a high likelihood of a record containing a code such that the record is assigned to the first group. Conversely, a probability or score below the second threshold may indicate a low likelihood of a record containing a code such that the record is assigned to the second group. In this example embodiment, a probability or score between the first and second thresholds designates an intermediate likelihood of a record containing a code and, depending upon the design of the system, can be assigned to either the first group or the second group, or may be assigned to a third group of records that are considered "unknown" in terms of whether the records are likely to contain a code.

During the training process as shown in block 43 of FIG. 3, the apparatus 20, such as the machine learning model 10, of an example embodiment is configured to adjust the threshold(s) that serve to define the first and second groups of records in order to achieve the desired accuracy requirements associated with the categorization of the records into the first and second groups. In this regard, threshold(s) may be defined and the machine learning model may then operate to categorize the records into the first and second groups. The apparatus, such as the machine learning model, then determines the accuracy of the categorization brought about by the predictions implemented by the machine learning model, such as by determining that the categorization is 90% accurate, 95% accurate, 99.9% accurate or the like. The accuracy of the categorization brought about by the predictions implemented by the machine learning model is then compared to a desired accuracy requirement. If the accuracy satisfies the desired accuracy requirement, the machine learning model may be considered to be trained and may thereafter be utilized to categorize records. However, if the accuracy fails to satisfy the desired accuracy requirement, the threshold(s) utilized by the machine learning model may be modified and the process may be repeated. The threshold(s) utilized by the machine learning model may be modified in various manners. For example, in an instance in which too many records were included in the first group and too few records were included in the second group, the threshold may be increased. Conversely, in an instance in which too few records were included in the first group and too many records were included in the second group, the threshold may be decreased. Although the training process is shown in block 43 of FIG. 3 to be performed upon the same data that is subsequently analyzed in conjunction with separating the records into first and second groups, the training of the machine learning model may be performed on different data and, as a result, may be performed prior to the input of the actual data into the machine learning model.

As shown in block 48, the apparatus 20 further includes means, such as the processing circuitry 22 or the like, for providing for subsequent processing of the records, such as in accordance with the threshold(s) that have been defined as described above. The subsequent processing differs depending upon whether the records are included in the first group of records or the second group of records. Although various types of subsequent processing of the first and second groups of records may be provided, the apparatus of an example embodiment depicted in FIG. 5 subsequently processes the records by assigning different audit responsibilities for the records depending upon their respective group. As shown in block 50 of FIG. 5, for example, the apparatus of this example embodiment includes means, such as the processing circuitry, the audit assignment circuitry 30, the input/output circuitry 28 or the like, for assigning different audit responsibility for the records depending upon whether the records are included in the first group of records or the second group of records. As shown in FIG. 1, for example, the apparatus, such as the audit assignment circuitry, of an example embodiment is configured to assign different audit responsibility by assigning audit responsibility for the first and second groups of records to the first and second auditors, respectively. As described above, the first and second groups of auditors may exhibit different performance characteristics with the first auditors providing improved performance relative to the second auditors. By assigning the first group of records that are more likely to support the addition of a code, such as an HCC code, to the first auditors who offer improved performance relative to the second auditors, the likelihood that those records that support the addition of a code, such as an HCC code, are identified and the content of the records is modified so as to be associated with the code is increased, while the risk that the more poorly performing second auditors will fail to identify a record that would support the addition of a code, such as an HCC code, is reduced because the second group of records that is reviewed by the second auditors is less likely to support the addition of a code, such as an HCC code, in the first instance as a result of the grouping of the records by the machine learning model 10.

Figure 5:
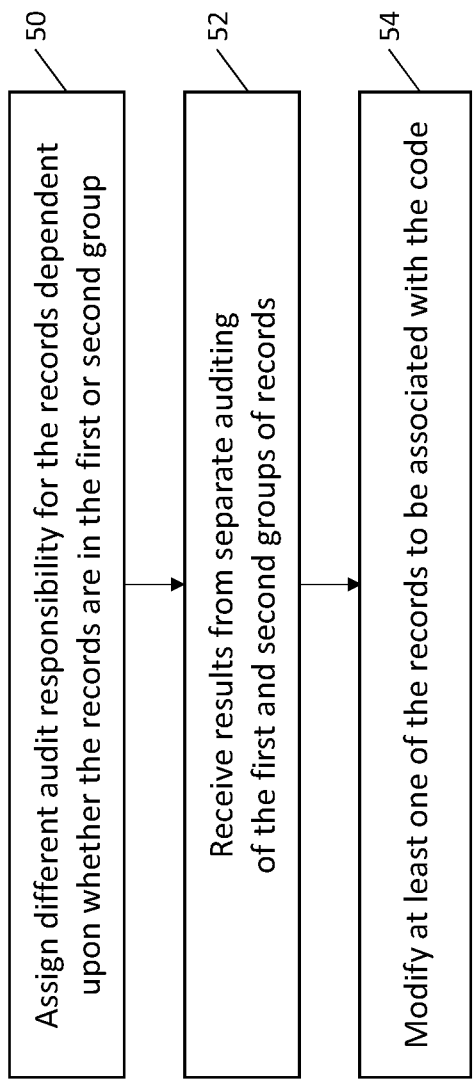
FIG. 5 is a flow chart illustrating the operations performed, such as by the apparatus of FIG. 2, in order to provide for different auditing of the records depending upon whether the records are included in the first or second groups in accordance with an example embodiment of the present disclosure.

In the example embodiment of FIG. 5 and as shown in block 52, the apparatus 20 also includes means, such as the processing circuitry 22, the record modification circuitry 32 or the like, for receiving results from the separate auditing of the first and second groups of records. These results may, for example, identify the record(s) that support the addition of a code, such as an HCC code. In response to the results from the auditing, the apparatus of this example embodiment also includes means, such as the record modification circuitry, the processing circuitry or the like, for modifying at least one of the records to be associated with the code, such as an HCC code. See block 54 of FIG. 5. In this regard, the apparatus, such as the record modification circuitry, may modify each of the records that have been identified by the auditor to support the addition of a code, such as an HCC code, to be associated with the code. In this regard, a new code may be added to the record itself or may otherwise be associated with the record, such as being linked to the record or the like.

As a result, the method, apparatus 20 and computer program product of an example embodiment provide for more consistent and accurate identification of the records with which a code should be associated, such as an HCC code, and thereafter correspondingly update the records to be associated with the code. As such, a healthcare benefit plan may be more appropriately compensated, such as by the government, for their patient population. In order to bring about this improved consistency with which medical records that should be associated with a code, such as an HCC code, are identified, the records are grouped by the method, apparatus and computer program product of an example embodiment based upon their likelihood of supporting the addition of a code, such as an HCC code, with the grouping being performed based upon data associated with the records, as opposed to the content of the records themselves. As such, the grouping may be performed, such as by machine learning model 10, in a more computationally efficient manner than if the content of the records themselves were reviewed during the grouping process.

Although the analysis of the records provided by the method, apparatus 20 and computer program product of an example embodiment may be performed for all records of a population, such as all medical records, the medical records for a patient having healthcare benefits provided by commercial insurer or other commercial healthcare plan may benefit more greatly than patients having only Medicare healthcare benefits. In this regard, the records for a patient associated with commercial healthcare payors are quite diverse in terms of the percentage of records with which an HCC code should be associated relative to the records that do not support the addition of an HCC code. In contrast, the medical records of patients having only Medicare healthcare coverage do not have such diversity and, instead, a substantially greater percentage of the records, such as 90% or so, support the addition of an HCC.

As such, for those records associated with patients having only Medicare healthcare coverage, it may be more efficient to simply audit all of the records since the vast majority will be found to support the addition of a code, such as an HCC code. Conversely, the medical records of patients having commercial healthcare coverage may benefit more greatly from the grouping of the records provided by the method, apparatus 20 and computer program product of an example embodiment in light of the greater diversity of the records in terms of the percentage of records that support the addition of a code, such as an HCC code, and the percentage of records that do not support the addition of a code, such as an HCC code. Thus, the apparatus of an example embodiment also include a means, such as filtration circuitry 34, processor circuitry 22 or the like, for excluding Medicare records from consideration prior to inputting the data into the machine learning mode 10. As such, the amount of data considered by the machine learning model while separating the records into the first and second groups may be further limited in order to increase the computational efficiency and decrease the computational time required for operation of the machine learning model.

FIGS. 3 and 5 illustrate flowcharts describing the operation of apparatuses, methods, and computer program products according to example embodiments of the invention. It will be understood that each block of the flowcharts, and combinations of blocks in the flowcharts, may be implemented by various means, embodied as hardware, firmware, circuitry, and/or other devices associated with execution of software including one or more software instructions. For example, one or more of the operations described above may be embodied by software instructions. In this regard, the software instructions which embody the procedures described above may be stored by a memory of an apparatus 20 employing an embodiment of the present invention and executed by processing circuitry 22 of the apparatus. As will be appreciated, any such software instructions may be loaded onto a computer or other programmable apparatus (e.g., hardware) to produce a machine, such that the resulting computer or other programmable apparatus implements the functions specified in the flowchart blocks. These software instructions may also be stored in a computer-readable memory that may direct a computer or other programmable apparatus to function in a particular manner, such that the software instructions stored in the computer-readable memory produce an article of manufacture, the execution of which implements the functions specified in the flowchart blocks. The software instructions may also be loaded onto a computer or other programmable apparatus to cause a series of operations to be performed on the computer or other programmable apparatus to produce a computer-implemented process such that the software instructions executed on the computer or other programmable apparatus provide operations for implementing the functions specified in the flowchart blocks.

The flowchart blocks support combinations of means for performing the specified functions and combinations of operations for performing the specified functions. It will be understood that one or more blocks of the flowcharts, and combinations of blocks in the flowcharts, can be implemented by special purpose hardware-based computer systems which perform the specified functions, or combinations of special purpose hardware and software instructions.

In some embodiments, some of the operations above may be modified or further amplified. Furthermore, in some embodiments, additional optional operations may be included. Modifications, amplifications, or additions to the operations above may be performed in any order and in any combination.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A method for grouping records based upon a prediction of content of the records, the method comprising:
   training a machine learning model using a training data set including features from a plurality of categories, the plurality of categories comprising principle and secondary diagnoses, procedures, and type of provider;
   receiving data associated with respective subjects of the records;
   inputting the data, but not content of the records, into the machine learning model that has been trained for a prediction as to whether respective records support addition of a code;
   in response to the prediction attributable to analyzing the data, but not the records, by the machine learning model, separating, using the machine learning model, the records into first and second groups with the first group including the records that the associated data indicates are more likely to support addition of the code and the second group including the records that the associated data indicates are less likely to support the addition of the code; and
   providing for subsequent processing of the records with the subsequent processing differing dependent upon whether the records are included in the first group of records or the second groups of records,
   wherein training the machine learning model comprises adjusting one or more thresholds utilized by the machine learning model in conjunction with the prediction as to whether respective records support the addition of the code in order to satisfy an accuracy requirement for categorization of the records.

2. A method according to claim 1 wherein providing for subsequent processing of the records comprises assigning, by audit assignment circuitry, different audit responsibility for the records depending upon whether the records are included in the first group of records or the second groups of records.

3. A method according to claim 2 wherein assigning different audit responsibility comprises assigning audit responsibility for the first and second groups of records to first and second auditors, respectively.

4. A method according to claim 2 further comprising:
   receiving results from separately auditing the first and second groups of records; and
   in response to the results from the auditing, modifying, by record modification circuitry, at least one of the records to be associated with the code.

5. A method according to claim 1 further comprising:
   splitting the records into multiple partitions across a distributed computing framework; and
   placing the machine learning model on each of a plurality of nodes of the distributed computing framework such that the machine learning model on a respective node analyzes records in a respective partition.

6. A method according to claim 1 wherein the records comprise medical records and the code comprises a Hierarchical Condition Category (HCC).

7. A method according to claim 6 wherein the data comprises payor data from one or more health care providers that includes one or more of claims information or summarized encounter information.

8. A method according to claim 6 further comprising excluding, by filtration circuitry, Medicare records from consideration prior to inputting the data into the machine learning model.

9. An apparatus, comprising:
   a processor; and
   a memory coupled to the processor and comprising computer readable program code embodied in the memory that is executable by the processor to perform operations comprising:
   training a machine learning model using a training data set including features from a plurality of categories, the plurality of categories comprising principle and secondary diagnoses, procedures, and type of provider;
   receiving data associated with respective subjects of the records;
   inputting the data, but not content of the records, into the machine learning model that has been trained for a prediction as to whether respective records support addition of a code;
   in response to the prediction attributable to analyzing the data, but not the records, by the machine learning model, separating, using the machine learning model, the records into first and second groups with the first group including the records that the associated data indicates are more likely to support addition of the code and the second group including the records that the associated data indicates are less likely to support the addition of the code; and
   providing for subsequent processing of the records with the subsequent processing differing dependent upon whether the records are included in the first group of records or the second groups of records,
   wherein training the machine learning model comprises adjusting one or more thresholds utilized by the machine learning model in conjunction with the prediction as to whether respective records support the addition of the code in order to satisfy an accuracy requirement for categorization of the records.

10. An apparatus according to claim 9 wherein providing for subsequent processing of the records comprises assigning different audit responsibility for the records depending upon whether the records are included in the first group of records or the second groups of records.

11. An apparatus according to claim 10 wherein assigning different audit responsibility comprises assigning different audit responsibility by assigning audit responsibility for the first and second groups of records to first and second auditors, respectively.

12. An apparatus according to claim 10 wherein the operations further comprise:
   receiving results from separately auditing the first and second groups of records; and
   in response to the results from the auditing, modifying at least one of the records to be associated with the code.

13. An apparatus according to claim 9 wherein the apparatus is embodied by a distributed computing framework, and wherein the operations further comprise:
   splitting the records into multiple partitions across the distributed computing framework, and wherein the machine learning model is placed on each of a plurality of nodes of the distributed computing framework such that the machine learning model on a respective node analyzes records in a respective partition.

14. An apparatus according to claim 9 wherein the records comprise medical records and the code comprises a Hierarchical Condition Category (HCC).

15. An apparatus according to claim 14 wherein the data comprises payor data from one or more health care providers that includes one or more of claims information or summarized encounter information.

16. An apparatus according to claim 14 wherein the operations further comprise:
excluding Medicare records from consideration prior to inputting the data into the machine learning model.

17. A computer program product comprising at least one non-transitory computer-readable storage medium for grouping records based upon a prediction of content of the records, the at least one non-transitory computer-readable storage medium storing software instructions that, when executed, cause an apparatus to perform operations comprising:
training a machine learning model using a training data set including features from a plurality of categories, the plurality of categories comprising principle and secondary diagnoses, procedures, and type of provider;
receiving data associated with respective subjects of the records;
inputting the data, but not content of the records, into the machine learning model that has been trained for a prediction as to whether respective records support addition of a code;
in response to the prediction attributable to analyzing the data, but not the records, by the machine learning model, separating, using the machine learning model, the records into first and second groups with the first group including the records that the associated data indicates are more likely to support addition of the code and the second group including the records that the associated data indicates are less likely to support the addition of the code; and
providing for subsequent processing of the records with the subsequent processing differing dependent upon whether the records are included in the first group of records or the second groups of records,
wherein training the machine learning model comprises adjusting one or more thresholds utilized by the machine learning model in conjunction with the prediction as to whether respective records support the addition of the code in order to satisfy an accuracy requirement for categorization of the records.

18. A computer program product according to claim 17 wherein providing for subsequent processing of the records comprises assigning different audit responsibility for the records depending upon whether the records are included in the first group of records or the second groups of records.

19. A computer program product according to claim 18 wherein the operations further comprise:
receiving results from separately auditing the first and second groups of records; and
in response to the results from the auditing, at least one of the records to include the code.

20. A computer program product according to claim 17 wherein the operations further comprise:
splitting the records into multiple partitions across a distributed computing framework; and
placing the machine learning model on each of a plurality of nodes of the distributed computing framework such that the machine learning model on a respective node analyzes records in a respective partition.

* * * * *